United States Patent
Kaur et al.

(10) Patent No.: US 10,100,136 B2
(45) Date of Patent: *Oct. 16, 2018

(54) ORGANOMETALLIC COMPOUND IN SOLID FORM, PROCESS FOR PREPARING THE SAME AND USE THEREOF

(71) Applicant: INDIAN OIL CORPORATION LIMITED, Mumbai, Maharashtra (IN)

(72) Inventors: Sukhdeep Kaur, Faridabad (IN); Gurmeet Singh, Faridabad (IN); Bhasker Bantu, Faridabad (IN); Naresh Kumar, Faridabad (IN); Gurpreet Singh Kapur, Faridabad (IN); Shashi Kant, Faridabad (IN); Biswajit Basu, Faridabad (IN); Ravinder Kumar Malhotra, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/371,193

(22) Filed: Dec. 6, 2016

(65) Prior Publication Data

US 2017/0081440 A1  Mar. 23, 2017

Related U.S. Application Data

(62) Division of application No. 14/416,609, filed as application No. PCT/IB2013/058797 on Sep. 24, 2013, now Pat. No. 9,587,041.

(30) Foreign Application Priority Data

Sep. 24, 2012 (IN) .......................... 2765/MUM/2012

(51) Int. Cl.
   *C08F 110/06* (2006.01)
   *C07F 3/02* (2006.01)
   (Continued)

(52) U.S. Cl.
   CPC .............. *C08F 110/06* (2013.01); *C07F 3/02* (2013.01); *C08F 4/16* (2013.01); *C08F 4/52* (2013.01)

(58) Field of Classification Search
   None
   See application file for complete search history.

(56) References Cited

U.S. PATENT DOCUMENTS

| | | | |
|---|---|---|---|
| 4,220,554 A | 9/1980 | Scatá et al. | |
| 4,727,051 A | 2/1988 | Breen et al. | |

(Continued)

FOREIGN PATENT DOCUMENTS

| | | |
|---|---|---|
| EP | 0 294 354 A2 | 12/1988 |
| EP | 1 273 595 A1 | 1/2003 |
| EP | 1 403 292 A1 | 3/2004 |

*Primary Examiner* — Catherine S Branch
(74) *Attorney, Agent, or Firm* — Maschoff Brennan

(57) ABSTRACT

The present invention provides a solid organomagnesium precursor having formula $\{Mg(OR')X\}.a\{MgX_2\}.b\{Mg(OR')_2\}.c\{R'OH\}$, wherein R' is selected from a hydrocarbon group, X is selected from a halide group, and a:b:c is in range of 0.01-0.5:0.01-0.5:0.01-5 and process for preparing the same, said process comprising contacting a magnesium source with a solvating agent, an organohalide and an alcohol to obtain the solid organomagnesium precursor. The present invention also provides a process for preparing a catalyst system using the organomagnesium precursor and its use thereof for polymerization of olefins.

11 Claims, 1 Drawing Sheet

(51) Int. Cl.
 *C08F 4/16* (2006.01)
 *C08F 4/52* (2006.01)

(56) References Cited

U.S. PATENT DOCUMENTS

| | | |
|---|---|---|
| 4,792,640 A | 12/1988 | Mehta |
| 4,820,672 A | 4/1989 | Mehta |
| 4,820,879 A | 4/1989 | Mehta |
| 5,081,320 A | 1/1992 | Wang et al. |
| 5,108,972 A | 4/1992 | Wang et al. |
| 5,414,158 A | 5/1995 | Gurtzgen |
| 7,135,531 B2 | 11/2006 | Zhu et al. |
| 2009/0306315 A1 | 12/2009 | Ramjoie et al. |

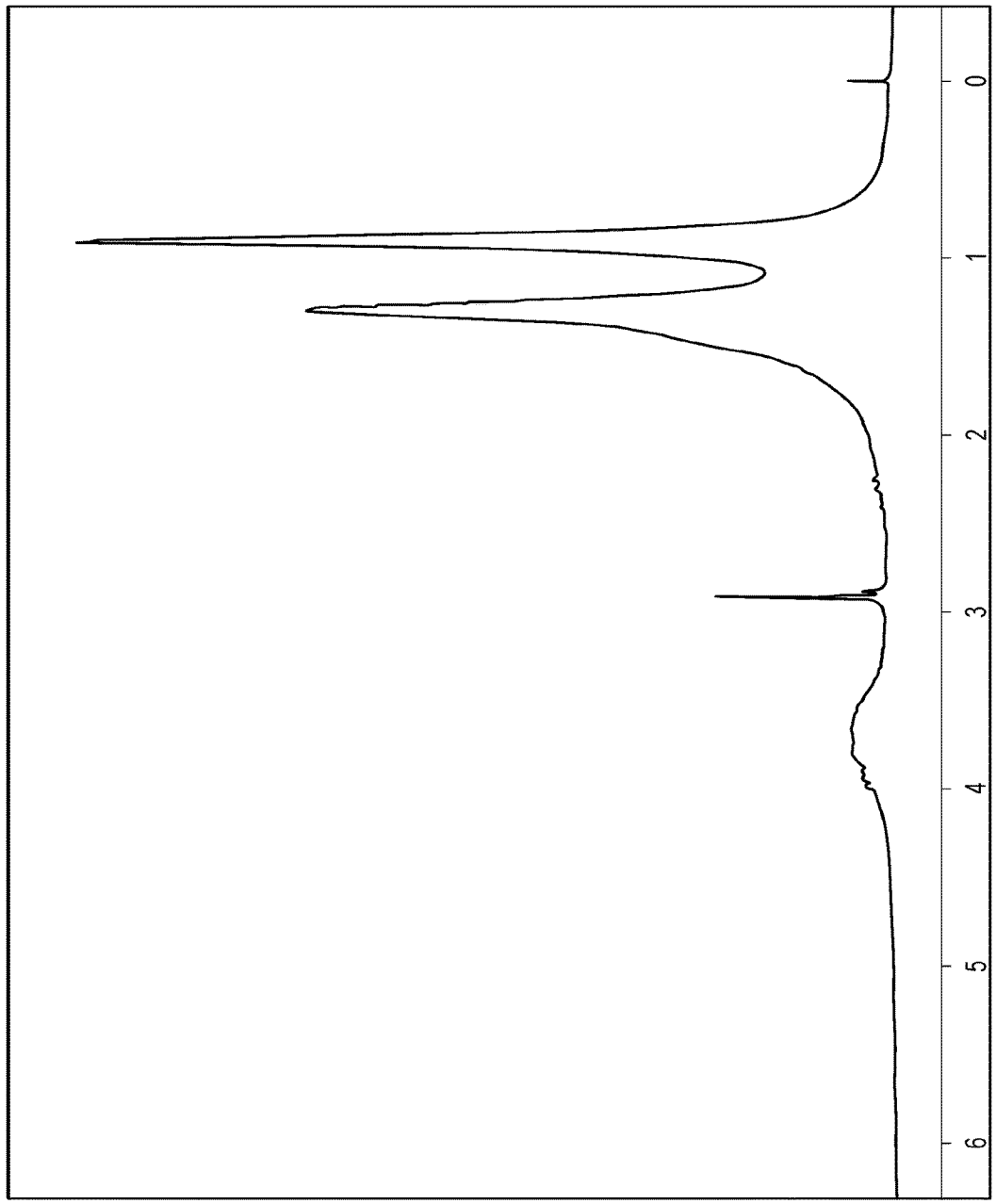

ORGANOMETALLIC COMPOUND IN SOLID FORM, PROCESS FOR PREPARING THE SAME AND USE THEREOF

CROSS-REFERENCE TO RELATED APPLICATIONS

This application is a divisional of U.S. patent application Ser. No. 14/416,609, which is the U.S. national phase of international patent application no. PCT/IB2013/058797, filed Sep. 24, 2013, which claims priority to Indian patent application no. 2765/MUM/2012 filed on Sep. 24, 2012. The foregoing patent applications are incorporated herein by reference.

FIELD OF INVENTION

The present invention relates to a catalyst system. More particularly, the present invention relates to a solid organomagnesium precursor for the catalyst system and process for preparing the same. The present invention also provides a process for preparing a catalyst system using the solid organomagnesium precursor and its use thereof for polymerization of olefins.

BACKGROUND OF INVENTION

Ziegler-Natta catalyst systems are well known for their capability to polymerize olefins. They in general consist of a support which mostly is magnesium based onto which titanium component has been added along with organic compound known as internal donor. This catalyst when combined with co-catalyst and/or external donor comprise of the complete ZN catalyst system.

Ziegler-Natta catalyst system typically consists of transition metal halide normally titanium halide supported on metal compound which is typically magnesium dichloride. Along with transition metal, there is an organic component known as internal electron donor that plays a typical role during catalyst synthesis and polymerization. $MgCl_2$ carrier, where the $MgCl_2$ is in active form, can be created by various methodologies. One of the methods is precipitating the $MgCl_2$ from an organic solution where magnesium is present as a soluble compound. The soluble magnesium compound can be achieved by starting from a magnesium alkyl and treating it with an alcohol. This step is then followed by chlorination of Mg alkyl or alkoxy compounds by a chlorination agent. The magnesium carrier can also be precipitated in the form of 'ready-made' $MgCl_2$. In that case the $MgCl_2$ has to be dissolved first in some suitable donor compound and then precipitated in hydrocarbon solvent. The $MgCl_2$ support material can also be precipitated by chlorinating a soluble magnesium alkyl compound simply by treating it with chlorine gas or hydrochloric acid. Once the desired specification of carrier is obtained, this is generally followed by titanation procedure which finally results in the catalyst synthesis.

U.S. Pat. No. 4,220,554 of Montedison describes the process of synthesizing the catalyst by treating Ti compounds with a spherical carrier which consists of Mg compound having the formula $X_nMg(OR)_{2-n}$. $X_nMg(OR)_{2-n}$ is synthesized by in reacting, in a single step, Mg metal, the organic halide and the orthosilicic acid ester. This product is isolated and then treated with halide of aromatic acid which is again isolated and treated with Ti compound for formation of catalyst. This catalyst is evaluated for propylene polymerization. This route applies the usage of orthosilicic ester for generation of magnesium alkoxy halide compound and focuses on the particle shape as well as size of the catalyst.

U.S. Pat. No. 4,727,051 of Stauffer Chemical Company discloses the process for synthesis of $X_nMg(OR)_{2-n}$ by preparing an alkanol adduct of a magnesium halide, reacting the product of this step with metallic magnesium, and drying the product. The compositions are then evaluated for as catalysts of olefin polymerization. The main disadvantage of this process is the usage of magnesium halides and large amount of alcohols.

U.S. Pat. No. 4,820,672 of Lithium Corporation of America describes the process for producing magnesium halide alcohol complex by reacting in an ether free hydrocarbon reaction medium, magnesium metal, dialkyl magnesium, alkyl magnesium halide, alkyl magnesium alkoxide, magnesium dialkoxide and alkoxy magnesium halide with an anhydrous hydrogen halide in the presence of chlorosubstituted alcohol. Further this complex is used for synthesis of ZN catalyst. The main disadvantage of this process is a large number of steps are involved for magnesium halide alcohol synthesis and further the usage of hydrogen halide which is difficult to handle. U.S. Pat. No. 4,820,879 further describes the process where alkoxy magnesium halides are formed by reacting preactivated magnesium with alcohol at higher temperatures and then treating it with hydrogen halides. Here also usage and handling of hydrogen halide is quite troublesome.

U.S. Pat. No. 4,792,640 discloses a process for synthesis of solid hydrocarbyloxymagnesium halides which is ether free, where preactivated (with iodine) magnesium metal is reacted with alkyl halide for some time and then addition of alcohol is done dropwise and finally refluxed. The solid product is filtered, dried and analyzed. Here the Grignard is stabilized in hydrocarbon. These patents contains no information on the activity of the ZN catalyst synthesized thereof.

U.S. Pat. No. 5,081,320 of Akzo NV describes the synthesis of alkoxymagnesium halides from secondary alcohol containing alkyl branching on the alpha carbon atom which is soluble in inert hydrocarbon. The process involves heating inert hydrocarbon solvent, secondary alcohol and ethanol with magnesium halide ($MgCl_2$) to dissolve the magnesium halide. Magnesium metal is then added along with additional solvent to prepare a soluble alkoxymagnesium halide. One disadvantage of this process is one need to prepare soluble magnesium alkoxide in order to further react the magnesium metal. U.S. Pat. No. 5,108,972 discloses the process of synthesis of alkoxymagnesium halide using non Grignard route where they react magnesium halide and magnesium alkoxide in excess of alcohol. Further magnesium source can also be added which is generated through dialkylmagnesium in hydrocarbon. Main disadvantage of this process is usage of expensive raw materials and large number of steps. The patent describes the process of synthesizing the magnesium compounds only.

U.S. Pat. No. 5,414,158 of Witco GmbH describes the one step synthesis of alkoxymagnesium halides in an inert hydrocarbon by reacting preactivated magnesium with small quantities of magnesium alkyl, with almost equimolar mixture of an alkyl halide and an alkanol. The obtained product is in excess of 90%. In this process first magnesium needs to be activated with magnesium alkyl at high temperature and then addition is carried out dropwise to the alkylhalide and alkanol mixture. One disadvantage of this process is requirement of expensive magnesium alkyl for activation which is also difficult to handle and further the extra addition of alkanol after the reaction to reduce viscosity. This patent describes the synthesis of alkoxymagnesium halide only and doesn't state the usage of the same as precursor for ZN catalyst.

EP1273595 of Borealis describes the process for synthesis of catalyst by reacting dialkylmagnesium with monohydric alcohol followed by dicarboxylic acid dihalide and chlorinated hydrocarbons. After washing and isolation of this product, it is further treated with titanium compound for the formation of ZN catalyst which shows activity for propylene polymerization. The main disadvantage of this process is usage of expensive dialkylmagnesium and its handling. This patent is mainly on the usage of emulsion stabilizer for controlling the particle size and shape.

U.S. Pat. No. 7,135,531 of BASF discloses the process for the synthesis of spherical catalyst which essentially contains titanium, internal donor and a support made from a magnesium compound, an alcohol, ether, a surfactant, and an alkyl silicate. The magnesium compound mainly magnesium dichloride is dissolve in alcohol at higher temperature and then treated with ether at lower temperature followed by addition of emulsifier at still lower temperature. This is then treated with silicate and titanium compound and final catalyst is ready after washing and drying. The main disadvantage of this process is higher alcohol content and expensive raw materials.

US2009/0306315 of SABIC discloses the process for preparing a polymerization catalyst which is synthesized by reacting $Mg(OR^1)_xCl_{2-x}$, which is obtained by reacting a Grignard compound with an alkoxy or aryloxy silane compound, with electron donor in the presence of inert dispersant to give an intermediate reaction product which is then treated with titanium halide to give the final catalyst which shows activity for olefin polymerization. This process has main disadvantage that its involves large number of steps which mainly consists of first solubilizing the magnesium compound and then solidifying before making final catalyst.

Thus, it would be desirable to provide a solid organometallic precursor compound for synthesis of a catalyst for polymerization of olefins that could be synthesized through a single step process using less expensive raw materials and lower alcohol content. Further, it would be desirable if the organometallic compound could be isolated, without any further purification and used as a precursor for making olefin polymerization catalyst which is highly active with low xylene solubility and excellent hydrogen response.

SUMMARY OF INVENTION

Accordingly the present invention provides a process for preparation of a solid organomagnesium precursor having formula $\{Mg(OR')X\}.a\{MgX_2\}.b\{Mg(OR')_2\}.c\{R'OH\}$, wherein R' is selected from a hydrocarbon group, X is selected from a halide group, and a:b:c is in range of 0.01-0.5:0.01-0.5:0.01-5, said process comprising contacting a magnesium source with a solvating agent, an organohalide and an alcohol to obtain the solid organomagnesium precursor.

The present invention also provides a process for preparation of a catalyst composition, said process comprises:

(a) contacting a solution of transition metal compound represented by $M(OR''')_pX_{4-p}$, where M is a transition metal and selected from Ti, V, Zr, and Hf; X is a halogen atom; R''' is a hydrocarbon group and p is an integer having value equal or less than 4 and where M is preferably titanium with the solid organomagnesium precursor having formula $\{Mg(OR')X\}.a\{MgX_2\}.b\{Mg(OR')_2\}.c\{R'OH\}$, wherein R' is selected from a hydrocarbon group, X is selected from a halide group, and a:b:c is in range of 0.01-0.5:0.01-0.5:0.01-5, to obtain the resulting solution and contact temperature of the solid organomagnesium precursor and the transition metal compound is between about −50° C. and about 150° C., and preferably between about −30° C. and about 120° C.;

(b) adding an internal donor either to the organomagnesium precursor component or to the titanium component and the contact time of the said component with the internal electron donor is either immediate or at least 1 minutes to 60 minutes at contact temperature of between about −50° C. and about 100° C., and preferably between about −30° C. and about 90° C.;

(c) treating the resulting solution obtained in the step (a) with a solution comprising a neat titanium component or a titanium component in a solvent and recovering a solid titanium catalyst component and maintaining the same at a temperature value in the range of 100 to 120° C. for about 10 to 60 minutes; and (d) optionally repeating step (c) for a predetermined number of times and then washed sufficiently with inert solvent at temperature 20° C. to 90° C. to obtain a solid catalysts composition.

The present invention also provides a process for preparation of a Ziegler-Natta catalyst system, said process comprising contacting the catalyst composition as obtained above with at least one cocatalyst, and at least one external electron donor to obtain a Ziegler-Natta catalyst system.

The present invention also provides a method of polymerizing and/or copolymerizing olefins, said method comprising the step of contacting an olefin having C2 to C20 carbon atoms under a polymerizing condition with the Ziegler-Natta catalyst system as obtained above.

BRIEF DESCRIPTION OF DRAWING

FIG. 1 illustrates NMR spectra for the compound $\{Mg(OR')X\}.a\{MgX_2\}.b\{Mg(OR')_2\}.c\{R'OH\}$.

DETAILED DESCRIPTION OF INVENTION

While the invention is susceptible to various modifications and alternative forms, specific embodiment thereof will be described in detail below. It should be understood, however that it is not intended to limit the invention to the particular forms disclosed, but on the contrary, the invention is to cover all modifications, equivalents, and alternative falling within the scope of the invention as defined by the appended claims.

The present invention discloses solid organometallic compound and a process of preparation of the solid organomagnesium compound. Further according to the present invention the organomagnesium compound acts as a precursor for Ziegler-Natta catalyst system and there is provided a process for synthesis of the catalyst system using the precursor thereof. Catalyst compositions and systems synthesized from organomagnesium compounds are able to polymerize olefins. The solid organomagnesium compound according to the present invention provides precursor based catalyst system has high activity, excellent hydrogen response, high selectivity and better co-monomer distribution.

According to the present invention, the solid organomagnesium compound is prepared by a single step process first by generating Grignard reagent followed by reacting with an alcohol. The isolated solid organomagnesium compound when contacted with metal compound M where M can be selected from Ti, V, Zr, Hf and along with the internal electron donors provide the catalyst system. The solid organomagnesium compound synthesis according to the present invention is achieved with reduced alcohol content without any further purification step. This catalyst system comprising of the said component have high activity for olefin polymerization with excellent hydrogen response and high stereospecificity.

Further, the present invention relates to the synthesis of Ziegler-Natta catalysts by using solid organomagnesium compound as a precursor. The Ziegler-Natta catalyst according to the present invention is prepared through precipitation, physical blending of solid mixtures, and in situ formation of halogenating agents. The resulting catalyst exhibits high activity for olefin polymerization with excellent hydrogen response.

Further, the invention provides a process of polymerizing and/or copolymerizing the olefin using the catalyst produced through the process mentioned in the invention.

Accordingly the present invention provides a process for preparation of a solid organomagnesium precursor having formula $\{Mg(OR')X\}.a\{MgX_2\}.b\{Mg(OR')_2\}.c\{R'OH\}$, wherein R' is selected from a hydrocarbon group, X is selected from a halide group, and a:b:c is in range of 0.01-0.5:0.01-0.5:0.01-5, said process comprising contacting a magnesium source with a solvating agent, an organohalide and an alcohol to obtain the solid organomagnesium precursor.

In one of the preferred embodiment, a solid organomagnesium precursor having formula $\{Mg(OR')X\}.a\{MgX_2\}.b\{Mg(OR')_2\}.c\{R'OH\}$, can be prepared as shown in below scheme 1:

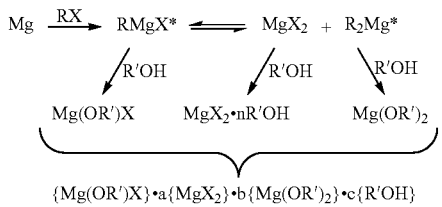

Scheme-1 wherein,
Mg—Magnesium Metal
RX—Alkyl Halide
RMgX—Grignard Reagent
*Intermediates
R'OH—Alcohol
Ratio of a:b:c is in range of 0.01-0.5:0.01-0.5:0.01-5
R and R' is selected from a hydrocarbon groups;
X is halogen selected from Cl, Br or I
n is an integer having value 1-10

According to the present invention, the process involves contacting magnesium source with organohalide compound and solvating agent for particular time and at particular temperature followed by reacting with alcohol. The magnesium source used in the present invention includes, not limited to, for example magnesium metal in form of powder, granules, ribbon, turnings, wire, blocks, lumps, chips; dialkylmagnesium compounds such as dimethylmagnesium, diethylmagnesium, diisopropylmagnesium, dibutylmagnesium, dihexylmagnesium, dioctylmagnesium, ethylbutylmagnesium, and butyloctylmagnesium; alkyl/aryl magnesium halides such as methylmagnesium chloride, ethylmagnesium chloride, isopropylmagnesium chloride, isobutylmagnesium chloride, tert-butylmagnesium chloride, benzylmagnesium chloride, methylmagnesium bromide, ethylmagnesium bromide, isopropylmagnesium bromide, isobutylmagnesium bromide, tert-butylmagnesium bromide, hexylmagnesium bromide, benzylmagnesium bromide, methylmagnesium iodide, ethylmagnesium iodide, isopropylmagnesium iodide, isobutylmagnesium iodide, tert-butylmagnesium iodide, and benzylmagnesium iodide. These magnesium compounds may be in the liquid or solid state. The magnesium compound is preferably magnesium metal.

In an embodiment of the present invention, the organohalide which is contacted with magnesium compound, includes, not limited to, for example alkyl halides such as methyl chloride, ethyl chloride, propyl chloride, isopropyl chloride, 1,1-dichloropropane, 1,2-dichloropropane, 1,3-dichloropropane, 2,3-dichloropropane, butyl chloride, 1,4-dichlorobutane, tert-butylchloride, amylchloride, tert-amylchloride, 2-chloropentane, 3-chloropentane, 1,5-dichloropentane, 1-chloro-8-iodoctane, 1-chloro-6-cyanohexane, cyclopentylchloride, cyclohexylchloride, chlorinated dodecane, chlorinated tetradecane, chlorinated eicosane, chlorinated pentacosane, chlorinated triacontane, iso-octyl chloride, 5-chloro-5-methyl decane, 9-chloro-9-ethyl-6-methyl eiscosane; halogenated alkyl benzene/benzylic halides, such as benzyl chloride and α,α' dichloro xylene; wherein the alkyl radical contains from about 10 to 15 carbon atoms, and the like as well as the corresponding bromine, fluorine and iodine substituted hydrocarbons. These organohalides may be used alone or in the form of mixture thereof. The organohalide is preferably benzyl chloride or butyl chloride or their mixtures thereof.

In an embodiment of the present invention, the solvating agent which stabilizes the Grignard, includes, not limited to, for example dimethyl ether, diethyl ether, dipropyl ether, diisopropyl ether, ethylmethyl ether, n-butylmethyl ether, n-butylethyl ether, di-n-butyl ether, di-isobutyl ether, isobutylmethyl ether, and isobutylethyl ether and the like. Also polar solvents, including but not limited to, dioxane, tetrahydrofuran, 2-methyl tetrahydrofuran, tetrahydropyran, chlorobenzene, dichloromethane and the like. Also nonpolar solvents like toluene, heptane, hexane, and the like. These solvating agents may be used alone or in the form of mixture thereof. The preferred solvating agent is diethyl ether or tetrahydrofuran or their mixture.

In an embodiment of the present invention, the components may be added in any order, highly preferably, magnesium followed by solvating agent, organohalide, and alcohol.

In an embodiment of the present invention, the reaction process can be done as single step such as reacting the components in one pot or multiple steps such as reacting magnesium, organic halide and solvating agent first and then addition of alcohol or reacting magnesium with solvating agent followed by addition of organic halide and alcohol, separately or as a mixture.

The quantity of organohalide depends upon the quantity of magnesium source used. According to the preferred embodiment, the magnesium source is reacted with the said organohalide in a molar ratio of between 1:20 to 1:0.2, preferably between about 1:10 to 1:0.5, more preferably, between 1:4 to 1:0.5. In another embodiment, the magnesium source and solvating agent are taken as molar ratio of between 1:20 to 1:0.2, preferably between about 1:15 to 1:1, more preferably, between 1:10 to 1:1. Another embodiment of the present invention, formation of homogeneous solution of magnesium component in solvating agent such as ether is desirable. For attaining this, the magnesium source, organohalide, solvating agent are contacted at temperature preferably between about −20° C. and about 200° C., and preferably between about −10° C. and about 140° C., more preferably between −10° C. to 100° C. Usually, the contact time is for about 0.5 to 12 h.

In an embodiment of the present invention, reaction promoters like iodine, the organohalides, inorganic halides such as CuCl, $MnCl_2$, AgCl, nitrogen halides like N-halide succinimides, trihaloisocynauric acid compounds, N-halophthalimide and hydrantoin compounds.

In an embodiment, the alcohol contacted includes, no limited to, for example, aliphatic alcohols such as methanol, ethanol, propanol, butanol, iso-butanol, t-butanol, n-pentanol, iso-pentanol, hexanol, 2-methylpentanol, 2-ethylbutanol, n-heptanol, n-octanol, 2-ethylhexanol, decanol and dodecanol, alicyclic alcohols such as cyclohexanol and methylcyclohexanol, aromatic alcohols such as benzyl alcohol and methylbenzyl alcohol, aliphatic alcohols containing an alkoxy group, such as ethyl glycol, butyl glycol; diols such as catechol, ethylene glycol, 1,3-propanediol, 1,4-butanediol, 1,5-pentanediol, 1,8-octanediol, 1,2-propanediol, 1,2-butanediol, 2,3-butanediol 1,3-butanediol, 1,2-pentanediol, p-menthane-3,8-diol, 2-methyl-2,4-pentanediol. The alcohols may be used alone or in the form of mixture thereof. The preferred alcohol is 2-ethyl-1-hexanol and its mixture thereof.

The quantity of alcohol depends upon the quantity of magnesium compound used. According to the preferred embodiment, the magnesium source along with organohalide is reacted with the said alcohol in a molar ratio of between 1:20 to 1:0.2, preferably between about 1:10 to 1:0.5, more preferably, between 1:4 to 1:0.5. In another embodiment of the present invention, formation of homogeneous solution of magnesium component in alcohol is desirable. For attaining this, the solution obtained by reacting magnesium compound, organohalide, in solvating agent is contacted with alcohol compound at temperature preferably between about 0° C. and about 150° C., and more preferably between about 10° C. and about 120° C. The preferred contact time according to the invention, is for about 0.5 to 12 h.

The present invention provides the process of preparation of stable solid organomagnesium compound. In an embodiment, the process involves contacting magnesium compound with organohalide compound and solvating agent for particular time and at particular temperature followed by reacting with alcohol. In an embodiment, the addition of organohalide, solvating agent and alcohol can be one shot, dropwise and/or controlled. In an embodiment, the resulting stable solid organomagnesium precursor solution can be isolated from solvating agent either using reduced pressure with and/or without heating, through precipitation, recrystallization. In another embodiment, the precipitated solid can be either used directly or in solution form for catalyst synthesis where in the solvent used for dissolving solid can be from the following group but not limited to polar and non polar aliphatic and/or aromatic hydrocarbons and combination thereof.

The present invention provides the process of preparation of stable solid organomagnesium compound. In an embodiment, the process involves contacting magnesium compound with organohalide compound and solvating agent for particular time and at particular temperature followed by reacting with alcohol. In an embodiment, the resulting organomagnesium compound can be dissolved in polar organic solvents and precipitated in organic solvents for examples not limiting to linear, branched, aromatic, cyclic, ring substituted, halide substituted alkanes and the likes, preferably non polar organic solvents or vice versa. In another embodiment, the precipitation methodology can be adopted during any stage of precursor synthesis for example but not limiting to, reacting magnesium with organic halide in solvating agent followed by precipitation in the mixture of alcohol and precipitating solvent or vice versa, or reacting magnesium with organic halide in solvating agent followed by addition of alcohol and then precipitating in precipitating solvent or vice versa.

Further, the present invention provides a catalyst composition. The catalyst composition includes combination of a magnesium moiety, other metal moiety and an internal donor. The magnesium moiety includes the stable solid organomagnesium compound of the present invention. The other metal moiety can be a main group metal or a transition metal, or a transition metal of IIIB-VIIIB element. In an embodiment, the transition metal is selected from, Ti, V, Zr and Hf, preferably, Ti.

In one of the embodiment, the present invention provides a process for preparation of a catalyst composition, said process comprises:

(a) contacting a solution of transition metal compound represented by $M(OR')_p X_{4-p}$), where M is a transition metal and is selected from a group comprising of Ti, V, Zr, and Hf, preferably Ti; X is a halogen atom; R''' is a hydrocarbon group and p is an integer having value equal or less than 4, with the solid organomagnesium precursor component of present invention to obtain a resulting solution and contact temperature of solid organomagnesium precursor and the transition metal compound is between about −50° C. and about 150° C., and preferably between about −30° C. and about 120° C.;

(b) adding an internal donor either to the solid organomagnesium precursor component or to the titanium component, preferably to organomagnesium compound; and the contact time of the said component with the internal electron donor immediate or is at least 1 minutes to 60 minutes at contact temperature of between about −50° C. and about 100° C., and preferably between about −30° C. and about 90° C.;

(c) treating the resulting solution obtained in the step (a) with a solution comprising a titanium component in a solvent and recovering a solid titanium catalyst component and maintaining the same at a temperature value in the range of 100 to 120° C. for about 10 to 60 minutes; and (d) optionally repeating step (c) for a predetermined number of times and then washed sufficiently with inert solvent at temperature 20° C. to 80° C. to obtain a solid catalysts composition.

In yet another embodiment of the present invention, the transition metal compound represented by $M(OR''')_p X_{4-p}$ is selected from a group comprising of transition metal tetrahalide, alkoxy transition metal trihalide/aryloxy transition metal trihalide, dialkoxy transition metal dihalide, trialkoxy transition metal monohalide, tetraalkoxy transition metal, and mixtures thereof; wherein:

(a) the transition metal tetrahalide is selected from a group comprising of titanium tetrachloride, titanium tetrabromide and titanium tetraiodide and the likes for V, Zr and Hf;

(b) alkoxy transition metal trihalide/aryloxy transition metal trihalide is selected from a group comprising of methoxytitanium trichloride, ethoxytitanium trichloride, butoxytitanium trichloride and phenoxytitanium trichloride and the likes for V, Zr and Hf;

(c) dialkoxy transition metal dihalide is diethoxy titanium dichloride and the likes for V, Zr and Hf;

(d) trialkoxy transition metal monohalide is triethoxy titanium chloride and the likes for V, Zr and Hf; and (e) tetraalkoxy transition metal is selected from a group comprising of tetrabutoxy titanium and tetraethoxy titanium and the likes for V, Zr and Hf.

The present invention also provides a process for preparation of a Ziegler-Natta catalyst system, said process comprising contacting the catalyst composition as obtained above with at least one cocatalyst, and at least one external electron donor to obtain a Ziegler-Natta catalyst system.

The present invention also provides a method of polymerizing and/or copolymerizing olefins, said method comprising the step of contacting an olefin having C2 to C20 carbon atoms under a polymerizing condition with the Ziegler-Natta catalyst system as obtained above.

The present invention provides the catalyst composition which includes combination of magnesium moiety, titanium moiety and an internal donor. The magnesium moiety includes the stable solid organomagnesium compound of the present invention. In an embodiment, the invention provides the method of synthesis of olefin polymerizing catalyst, comprising of reacting the organomagnesium compound with liquid titanium compound which includes tetravalent titanium compound represented as $Ti(OR)_p X_{4-p}$ where X can be halogen selected from Cl or Br or I, R is a hydrocarbon group and p is an integer varying from 0-4. Specific examples of the titanium compound include, not limited to titanium tetrahalides such as titanium tetrachloride, titanium tetrabromide, titanium tetraiodide; alkoxytitanium trihalide/ aryloxytitanium trihalide such as methoxytitanium trichloride, ethoxytitanium trichloride, butoxytitanium trichloride, phenoxytitanium trichloride; di alkoxy titanium dihalides such as diethoxy titanium dichloride; trialkoxytitanium monohalide such as triethoxy titanium chloride; and tetraalkoxytitanium such as tetrabutoxy titanium, tetraethoxy titanium, and mixtures thereof, with titanium tetrachloride being preferred. The titanium compounds may be used alone or in the form of mixture thereof.

According to the present invention, the magnesium moiety includes the stable solid organomagnesium compound. In an embodiment, the contact of organomagnesium compound with titanium compound can be either neat or in solvent which can be chlorinated or non chlorinated aromatic or aliphatic in nature examples not limiting to benzene, decane, kerosene, ethyl benzene, chlorobenzene, dichlorobenzene, toluene, o-chlorotoluene, xylene, dichloromethane, chloroform, cyclohexane and the like, comprising from 5 to 95 volume percent. In another embodiment, the stable solid organomagnesium compound can be used as solid or in solvent which can be chlorinated or non chlorinated aromatic or aliphatic in nature examples not limiting to benzene, decane, kerosene, ethyl benzene, chlorobenzene, dichlorobenzene, toluene, o-chlorotoluene, xylene, dichloromethane, chloroform, cyclohexane and the like, comprising from 5 to 95 volume percent.

In an embodiment, either the titanium compound is added to the organomagnesium compound or vice-verse, preferably, organomagnesium compound is added to titanium compound.

In another embodiment, this addition is either one shot or dropwise or controlled. In another embodiment, the contact temperature of organomagnesium and titanium compound is preferably between about −50° C. and about 150° C., and more preferably between about −30° C. and about 120° C.

The liquid titanium compound helps in the formation of amorphous $MgCl_2$ as it acts as halogenating agent as well as is dispersed and supported on the catalyst surface. Moreover, the removal of alkoxy group from the solution, results in the precipitation of the solid component, having especially desired surface properties and particle shape. More important, the particles are uniform in shape. In an embodiment, the titanium compound is added in amounts ranging from usually about at least 1 to 200 moles, preferably, 3 to 200 moles and more preferably, 5 mole to 100 moles, with respect to one mole of magnesium.

While preparing the catalyst composition, magnesium component is contacted with the titanium component along with the internal donor to get the solid titanium component. In one embodiment, magnesium and titanium component can be made to come in contact with the internal electron donor.

In another embodiment, the solid titanium catalyst component is made by contacting a magnesium compound and a titanium compound in the presence of an internal electron donor compound.

In still another embodiment, the solid titanium catalyst component is made by forming a magnesium based catalyst support optionally with the titanium compound and optionally with the internal electron donor compound, and contacting the magnesium based catalyst support with the titanium compound and the internal electron donor compound.

The present invention provides the catalyst composition which includes combination of magnesium moiety, titanium moiety and an internal donor. The magnesium moiety includes the stable solid organomagnesium compound. In an embodiment, internal electron donor is selected from phthalates, benzoates, diethers, succinates, malonates, carbonates, and combinations thereof. Specific examples include, but are not limited to di-n-butyl phthalate, di-i-butyl phthalate, di-2-ethylhexyl phthalate, di-n-octyl phthalate, di-i octyl phthalate, di-n-nonyl phthalate, methyl benzoate, ethyl benzoate, propyl benzoate, phenyl benzoate, cyclohexyl benzoate, methyl toluate, ethyl toluate, p-ethoxy ethyl benzoate, p-isopropoxy ethyl benzoate, diethyl succinate, di-propyl succinate, diisopropyl succinate, dibutyl succinate, diisobutyl succinate, diethyl malonate, diethyl ethylmalonate, diethyl propyl malonate, diethyl isopropylmalonate, diethyl butylmalonate, diethyl 1,2-cyclohexanedicarboxylate, di-2-ethylhexyl 1,2-cyclohexanedicarboxylate, di-2-isononyl 1,2-cyclohexanedicarboxylate, methyl anisate, ethyl anisate and diether compounds such as 9,9-bis(methoxymethyl) fluorene, 2-isopropyl-2-isopentyl-1,3-dimethoxypropane, 2,2-diisobutyl-1,3-dimethoxypropane, 2,2-diisopentyl-1,3-dimethoxypropane, 2-isopropyl-2-cyclohexyl-1,3-dimethoxypropane, preferably di-iso-butyl phthalate.

The "internal electron donor" is a compound that is added during the formation of catalyst composition where it is acting as Lewis base i.e. donating the electron pairs to the metal present in the catalyst composition. The internal electron donor stabilizes the primary crystallites of magnesium dihalide which is generated in-situ. Apart from this, the internal donor also being better Lewis base have preferred coordination with the higher acidity coordination sites on magnesium dihalide matrix which in turn avoid the coordination of titanium and hence prevents the formation of inactive sites. They also increase the activity of low active sites. This in all enhances the catalyst stereoselectivity. All internal electron donor compounds commonly used in the art can be used in the present invention. In another embodiment, the internal electron donor is used in an amount of from 0 to 1 moles, preferably from 0.01 to 0.5 moles, with respect to one mole of magnesium.

The present invention provides the catalyst composition which includes combination of magnesium moiety, titanium moiety and an internal donor. The magnesium moiety includes the solid organomagnesium compound. In an embodiment, the addition of internal is either to the organomagnesium compound or to the titanium component, preferably to organomagnesium compound. The contact temperature of internal donor depends upon to which component it is being added. In an embodiment, the contact time of the desired component with the internal electron donor is either immediate or at least 1 minutes to 60 minutes at contact temperature of preferably between about −50° C. and about 100° C., and more preferably between about −30° C. and about 90° C. in another embodiment, the internal donor may be added in single step or in multiple steps.

The contact procedure for titanium and magnesium component is slowly with dropwise addition at desired temperature and then heated to activate the reaction between both the components.

In a preferred embodiment, this reaction system is gradually heated to the temperature effective to carry out the reaction, preferably about −50° C. and about 150° C., and more preferably about −30° C. and about 120° C., and heating is instigated at a rate of 0.1 to 10.0° C./minute, or at a rate of 1 to 5.0° C./minute. The resultant is the solid component in the solvent comprising of magnesium, titanium and halogen components.

The procedure of contacting the titanium component may be repeated one, two, three or more times as desired. In an embodiment, the resulting solid material recovered from the mixture can be contacted one or more times with the mixture of liquid titanium component in solvent for at least 10 minutes up to 60 minutes, at temperature from about 25° C. to about 150° C., preferably from about 30° C. to about 110° C.

The resulting solid component comprising of magnesium, titanium, halogen, alcohol and the internal electron donor can be separated from the reaction mixture either by filtration or decantation and finally washed with inert solvent to remove unreacted titanium component and other side products. Usually, the resultant solid material is washed one or more times with inert solvent which is typically a hydrocarbon including, not limiting to aliphatic hydrocarbon like isopentane, isooctane, hexane, pentane or isohexane. In an embodiment, the resulting solid mixture is washed one or more times with inert hydrocarbon based solvent preferably, hexane at temperature from about 20° C. to about 80° C., preferably from about 25° C. to about 70° C. The solid catalyst can be separated and dried or slurried in a hydrocarbon specifically heavy hydrocarbon such as mineral oil for further storage or use.

In an embodiment, the catalyst composition includes from about 2.0 wt % to 20 wt % of internal electron donor, titanium is from about 0.5 wt % to 10.0 wt % and magnesium is from about 10 wt % to 20 wt %.

The present invention provides the catalyst system for polymerization of olefins. In the embodiment, the method of polymerization process is provided where the catalyst system is contacted with olefin under polymerization conditions. The catalyst system includes catalyst composition, organoaluminum compounds and external electron donors. The catalyst composition includes combination of magnesium moiety, titanium moiety and an internal donor. The magnesium moiety includes the stable solid organomagnesium compound.

Further, the present invention provides a method of polymerizing and/or copolymerizing olefins where the catalyst system is contacted with olefin under polymerization conditions. The catalyst system includes catalyst composition, cocatalyst and external electron donors. The catalyst composition includes combination of magnesium moiety, titanium moiety and an internal donor. The magnesium moiety includes the stable solid organomagnesium compound. The co-catalyst may include hydrides, organoaluminum, lithium, zinc, tin, cadmium, beryllium, magnesium, and combinations thereof. In an embodiment, the preferred co-catalyst is organoaluminum compounds.

In another embodiment the catalyst system includes catalyst composition, organoaluminum compounds and external electron donors. The catalyst composition includes combination of magnesium moiety, titanium moiety and an internal donor. The magnesium moiety includes the stable solid organomagnesium compound.

The olefins according to the present invention includes from C2-C20. The ratio of titanium (from catalyst composition):aluminum (from organoaluminum compound):external donor can be from 1:5-1000:0-250, preferably in the range from 1:25-500:25-100.

The present invention provides the catalyst system. The catalyst system includes catalyst component, organoaluminum compounds and external electron donors. In an embodiment, the organoaluminum compounds include, not limiting, alkylaluminums such as trialkylaluminum such as preferably triethylaluminum, triisopropylaluminum, triisobutylaluminum, tri-n-butylaluminum, tri-n-hexylaluminum, tri-n-octylaluminum; trialkenylaluminums such as triisoprenyl aluminum; dialkylaluminum halides such as diethylaluminum chloride, dibutylaluminum chloride, diisobutylaluminum chloride and diethyl aluminum bromide; alkylaluminum sesquihalides such as ethylaluminum sesquichloride, butylaluminum sesquichloride and ethyl aluminum sesquibromide; dialkylaluminum hydrides such as diethylaluminum hydride and dibutylaluminum hydride; partially hydrogenated alkylaluminum such as ethylaluminum dihydride and propylaluminum dihydride and aluminoxane such as methylaluminoxane, isobutylaluminoxane, tetraethylaluminoxane and tetraisobutylaluminoxane; diethylaluminum ethoxide.

The mole ratio of aluminum to titanium is from about 5:1 to about 1000:1 or from about 10:1 to about 700:1, or from about 25:1 to about 500:1.

The present invention provides the catalyst system. The catalyst system includes catalyst component, organoaluminum compounds and external electron donors. The external electron donors are organosilicon compounds, diethers and alkoxy benzoates. The external electron donor for olefin polymerization when added to the catalytic system as a part of co-catalyst retains the stereospecificity of the active sites, convert non-stereospecific sites to stereospecific sites, poisons the non-stereospecific sites and also controls the molecular weight distributions while retaining high performance with respect to catalytic activity. The external electron donors which are generally organosilicon compounds includes but are not limited to trimethylmethoxysilane, trimethylethoxysilane, dimethyldimethoxysilane, dimethyldiethoxysilane, diisopropyldimethoxysilane, diisobutyldimethoxysilane, t-butylmethyldimethoxy silane, t-butylmethyldiethoxysilane, t-amylmethyldiethoxysilane, dicyclopentyldimethoxysilane, diphenyldimethoxysilane, phenylmethyldimethoxysilane, diphenyldiethoxysilane, bis-o-tolydimethoxysilane, bis-m-tolydimethoxysilane, bis-p-tolydimethoxysilane, bis-p-tolydimethoxysilane, bisethylphenyldimethoxysilane, dicyclohexyldimethoxysilane, cyclohexylmethyldimethoxysilane, cyclohexylmethyldiethoxysilane, ethyltrimethoxysilane, ethyltriethoxysilane, vinyltrimethoxysilane, methyltrimethoxysilane, n-propyltriethoxysilane, decyltrimethoxysilane, decyltriethoxysilane, phenyltrimethoxysilane, gamma-chloropropyltrimethoxysilane, methyltriethoxysilane, ethyltriethoxysilane, vinyltriethoxysilane, t-butyltriethoxysilane, n-butyltriethoxysilane, iso-butyltriethoxysilane, phenyltriethoxysilane, gamma-aminopropyltriethoxysilane, cholotriethoxysilane, ethyltriisopropoxysilane, vinyltirbutoxysilane, cyclohexyltrimethoxysilane, cyclohexyltriethoxysilane, 2-norbornanetrimethoxysilane, 2-norbornanetriethoxysilane, 2-norbornanemethyldimethoxysilane, ethyl silicate, butyl silicate, trimethylphenoxysilane, and methyltriallyloxysilane, cyclopropyltrimethoxysilane, cyclobutyltrimethoxysilane, cyclopentyltrimethoxysilane, 2-methylcyclopentyltrimethoxysilane, 2,3-dimethylcyclopentyltrimethoxysilane, 2,5-dimethylcyclopentyltrimethoxysilane, cyclopentyltriethoxysilane, cyclopentenyltrimethoxysilane, 3-cyclopentenyltrimethoxysilane, 2,4-cyclopentadienyltrimethoxysilane, indenyltrimethoxysilane and fluorenyltrimethoxysilane; dialkoxysilanes such as dicyclopentyldimethoxysilane, bis(2-methylcyclopentyl)dimethoxysilane, bis(3-tertiary butylcyclopentyl)dimethoxysilane, bis(2,3-dimethylcyclopentyl)dimethoxysilane, bis(2,5-dimethylcyclopentyl)dimethoxysilane, dicyclopentyldiethoxysilane, dicyclobutyldiethoxysilane, cyclopropylcyclobutyldiethoxysilane, dicyclopentenyldimethoxysilane, di(3-cyclopentenyl)dimethoxysilane, bis(2,5-dimethyl-3-cyclopentenyl)dimethoxysilane, di-2,4-cyclopentadienyl)dimethoxysilane, bis(2,5-dimethyl-2,4-cyclopentadienyl)dimethoxysilane, bis(1-methyl-1-cyclopentylethyl)dimethoxysilane, cyclopentylcyclopentenyldimethoxysilane, cyclopentylcyclopentadienyldimethoxysilane, diindenyldimethoxysilane, bis(1,3-dimethyl-2-indenyl)dimethoxysilane, cyclopentadienylindenyldimethoxysilane, difluorenyldimethoxysilane, cyclopentylfluorenyldimethoxysilane and indenylfluorenyldimethoxysilane; monoalkoxysilanes such as tricyclopentylmethoxysilane, tricyclopentenylmethoxysilane, tricyclopentadienylmethoxysilane, tricyclopentylethoxysilane, cyclopentylmethylmthoxysilane, dicyclopentylethylmethoxysilane, dicyclopentylmethylethoxysilane, cyclopentyldimethylmethoxysilane, cyclopentyldiethylmethoxysilane, cyclopentyldimethylethoxysilane, bis(2,5-dimethylcyclopentyl)cyclopentylmethoxysilane, dicyclopentylcyclopentenylmethoxysilane, dicyclopentylcyclopentenadienylmethoxysilane, diindenylcyclopentylmethoxysilane and ethylenebis-cyclopentyldimethoxysilane; aminosilanes such as aminopropyltriethoxysilane, n-(3-triethoxysilylpropyl)amine, bis [(3-triethoxysilyl)propyl]amine, aminopropyltrimethoxysilane, aminopropylmethyldiethoxysilane, hexanediaminopropyltrimethoxysilane.

In an embodiment, the external electron donor, other than organosilicon compounds include, but not limited to amine, diether, esters, carboxylate, ketone, amide, phosphine, carbamate, phosphate, sulfonate, sulfone and/or sulphoxide.

The external electron donor is used in such an amount to give a molar ratio of organoaluminum compound to the said external donor from about 0.1 to 500, preferably from 1 to 300.

In the present invention, the polymerization of olefins is carried out in the presence of the catalyst system described above. The catalyst system is contacted with olefin under polymerization conditions to produce desired polymer products. The polymerization process can be carried out such as by slurry polymerization using an inert hydrocarbon solvent as a diluent, or bulk polymerization using the liquid monomer as a reaction medium and in gas-phase operating in one or more fluidized or mechanically agitated bed reactors. In an embodiment, polymerization is carried out as such. In another embodiment, the copolymerization is carried out using at least two polymerization zones.

The catalyst of the invention can be used in the polymerization of the above-defined olefin $CH_2=CHR$, the examples of said olefin include ethylene, propylene, 1-butene, 4-methyl-1-pentene, 1-hexene, and 1-octene.

In particular, said catalyst can be used to produce, the following products such as high-density polyethylene (HDPE, having a density higher than 0.940 g/cm3), which includes ethylene homopolymer and copolymer of ethylene and α-olefins having 3 to 12 carbon atoms; linear low-density polyethylene (LLDPE, having a density lower than 0.940 g/cm$^3$), and very low density and ultra low density polyethylene (VLDPE and ULDPE, having a density lower than 0.920 g/cm3, and as low as 0.880 g/cm3), consisting of the copolymer of ethylene and one or more α-olefins having 3 to 12 carbon atoms, wherein the molar content of the unit derived from ethylene is higher than 80%; elastomeric copolymer of ethylene and propylene, and elastomeric terpolymers of ethylene, propylene and butene-1 as well as diolefins at a small ratio, wherein the weight content of the unit derived from ethylene is between about 30% and 70%; isotactic polypropylene and crystalline copolymer of propylene and ethylene and/or other α-olefins, wherein the content of the unit derived from propylene is higher than 85% by weight (random copolymer); impact propylene polymer, which are produced by sequential polymerization of propylene and the mixture of propylene and ethylene, with the content of ethylene being up to 40% by weight; copolymer of propylene and 1-butene, containing a great amount, such as from 10 to 40 percent by weight, of unit derived from 1-butene. It is especially significant that the propylene polymers produced by using the catalysts of the invention have high isotactic index.

The polymerization is carried out at a temperature from 20 to 120° C., preferably from 40 to 80° C. When the polymerization is carried out in gas phase, operation pressure is usually in the range of from 5 to 100 bar preferably from 10 to 50 bar. The operation pressure in bulk polymerization is usually in the range of from 10 to 150 bar, preferably from 15 to 50 bar. The operation pressure in slurry polymerization is usually in the range of from 1 to 10 bar, preferably from 2 to 7 bar. Hydrogen can be used to control the molecular weight of polymers.

In the present invention, the polymerization of olefins is carried out in the presence of the catalyst system described in the invention. The described catalyst can be directly added to the reactor for polymerization or can be prepolymerized i.e. catalyst is subjected to a polymerization at lower conversion extent before being added to polymerization reactor. Prepolymerization can be performed with olefins preferably ethylene and/or propylene where the conversion is controlled in the range from 0.2 to 500 gram polymer per gram catalyst. In the present invention, the polymerization of olefins in presence of the described catalyst system leads to the formation of polyolefins having xylene solubility (XS) ranging from about 0.2% to about 15%. In another embodiment, polyolefins have xylene solubility (XS) from about 2% to about 8%. Here XS refers to the weight percent of polymer that get dissolves into hot xylene generally for measuring the tacticity index such as highly isotactic polymer will have low XS % value i.e. higher crystallinity, whereas low isotactic polymer will have high XS % value.

In an embodiment of the invention, the catalyst efficiency (measured as kilogram of polymer produced per gram of catalyst) of the described catalyst system is at least about 30. In another embodiment, the catalyst efficiency of the described catalyst system is at least about 60.

The present invention provides the catalyst system. The catalysts system when polymerizes olefins provides polyolefins having melt flow indexes (MFI) of about 0.1 to about 100 which is measured according to ASTM standard D1238. In an embodiment, polyolefins having MFI from about 0.5 to about 30 are produced.

The present invention provides the catalyst system. The catalysts system when polymerizes olefins provides polyolefins having bulk densities (BD) of at least about 0.3 cc/g.

The following non-limiting examples illustrate in details about the invention. However, they are, not intended to be limiting the scope of present invention in any way.

Example 1

Preparation of Organomagnesium Compound

In 500 ml glass reactor maintained at 0° C., calculated amount of magnesium (powder or turnings) were weighed and added into the reactor followed by diethyl ether followed by addition of calculated amount of organohalide. This mixture was stirred and after the activation of the reaction, the mixture was allowed to be maintained at same temperature until all magnesium has reacted. To the resulting solution, the calculated amount of alcohol was added dropwise over a period of 1-2 h. After the completion of addition, the solution was allowed to stir for another 0.5 h. Finally, the ether was evaporated and solid compound was analyzed.

The organomagnesium compounds synthesized by the above procedure have been tabulated in Table 1.

TABLE 1

| Precursor | Mg Ratio | Benzyl chloride Ratio | BuCl Ratio | Alcohol Ratio | Solvent | Alcohol | Mg (wt %) | Cl (wt %) | Remark |
|---|---|---|---|---|---|---|---|---|---|
| MGP#25 | 1.3 | 1 | 0 | 0 | DEE | — | 12.6 | 18.7 | |
| MGP#27 | 1$^a$ | 0 | 0 | 1 | DEE | EHA | 12.6 | 18.7 | $^a$MGP#25 as starting material |
| MGP#37 | 1 | 1.1 | 0 | 1 | DEE | EHA | 12.7 | 18.8 | |
| MGP#42 | 1 | 1.1 | 0 | 1 | DEE | Benzyl Alcohol | 14.5 | 21.2 | |
| MGP#43 | 1 | 0 | 1.1 | 1 | DEE | EHA | 12.6 | 18.7 | |
| MGP#45 | 1 | 1.1 | 0 | 1 | DEE | isobutanol | 18.2 | 26.7 | |
| MGP#53 | 1 | 1.1 | 0 | 1 | DEE | Catechol | 21.2 | 30.9 | |
| MGP#57 | 1 | 1.1 | 0 | 1 | DEE | Cresol | 14.5 | 21.1 | |
| MGP#61 | 1 | 1.1 | 0 | 1 | DEE | EHA | 12.5 | 18.9 | |
| MGP#63 | 1 | 1.1 | 0 | 1 | DEE/toluene (20:80) | EHA | | | |
| MGP#64 | 1 | 1.1 | 0 | 1 | DEE | isobutanol | 17.1 | 25.2 | Isobutanol/hexane used as precipitating agent |
| MGP#66 | 1 | 1.1 | 0 | 1 | DEE | EHA | 12.7 | 18.9 | |
| MGP#67 | 1 | 0 | 1.1 | 1 | DEE | EHA | 12.5 | 18.9 | |
| MGP#68 | 1 | 1.1 | 0 | 1 | DEE | EHA | 12.5 | 18.7 | |
| MGP#73 | 1 | 1.1 | 0 | 1 | DEE | 3-methoxy-1-butanol | 12.4 | 18.7 | |
| MGP#74 | 1 | 1.1 | 0 | 1 | DEE | 3-methoxy-1-butanol | 12.5 | 18.5 | |
| MGP#75 | 1 | 1.1 | 0 | 1 | DEE | EHA | 12.5 | 18.7 | |
| MGP#76 | 1 | 1.1 | 0 | 1 | DEE | EHA | 12.7 | 18.9 | |
| MGP#83 | 1 | 0 | 1.1 | 1 | DEE/chlorobenzene | EHA | 12.5 | 18.5 | |
| MGP#84 | 1 | 1.1 | 0 | 1 | DEE/chlorobenzene | EHA | 12.5 | 18.7 | |
| MGP#85 | 1 | 1.1 | 0 | 1 | DEE/chlorobenzene | EHA | 12.6 | 18.7 | |
| MGP#87 | 1 | 1.1 | 0 | 1 | DEE | EHA | 12.7 | 18.5 | |
| MGP#88 | 1 | 1.1 | 0 | 1 | DEE | EHA | 12.6 | 18.9 | |
| MGP#90 | 1 | 1.1 | 0 | 1 | DEE | EHA | 12.5 | 18.6 | |
| MGP#91 | 1 | 1.1 | 0 | 1 | DEE | EHA | 12.6 | 18.5 | |
| MGP#92 | 1 | 0 | 1.1 | 1 | DEE | EHA | 12.6 | 18.6 | Reaction @ 30° C. |
| MGP#93 | 1 | 1.1 | 0 | 1 | DEE | EHA | 12.5 | 18.5 | EHA addition @ 0° C. |
| MGP#94 | 1 | 1.1 | 0 | 1 | DEE | EHA | 12.7 | 18.5 | |
| MGP#95 | 1 | 1.1 | 0 | 1 | DEE | EHA | 12.6 | 18.9 | Reaction @ 30° C. |

TABLE 1-continued

| Precursor | Mg Ratio | Benzyl chloride Ratio | BuCl Ratio | Alcohol Ratio | Solvent | Alcohol | Mg (wt %) | Cl (wt %) | Remark |
|---|---|---|---|---|---|---|---|---|---|
| MGP#96 | 1 | 1.1 | 0 | 1 | DEE | EHA | 12.4 | 18.6 | |
| MGP#97 | 1 | 1.1 | 0 | 1 | DEE | EHA | 12.6 | 18.9 | |
| MGP#137 | 1 | 1.1 | 0 | 1 | DEE | EHA | 12.5 | 18.7 | Benzyl chloride/ EHA mixture added |

EHA = 2-ethyl-1-hexanol;
DEE = diethyl ether

Table 1 represents the conditions for preparation of the solid organomagnesium compound using different alcohols and organohalides under different reaction conditions.

Example 2

Preparation of the Catalyst Component

To 60 ml of TiCl$_4$ solution maintained at desired temperature, added 100 ml of the organomagnesium precursor along with internal donor (ID/Mg=0.11 moles) over a period of 10 min and stirred. After the system has attained the desired temperature, the resultant solution was maintained at the same temperature for 15 min. The resultant solution was clear orange in color. Gradually the reaction temperature was increased to 110° C. and maintained for 1 h. After settling and decantation, the suspended solid was again treated with 60 ml TiCl$_4$ and 60 ml chlorobenzene and after temperature reached 110° C., the mixture was maintained under stirring for 15 minutes. The above step was again repeated. After the reaction was finished, the solid was decanted and washed sufficiently with hexane at 70° C., respectively and further dried under hot nitrogen till freely flowing.

The solid catalysts composition synthesized by the above procedure has been tabulated in Table 2.

TABLE 2

| Catalyst | Precursor | Precursor & TiCl$_4$ contact temperature ° C. | Internal donor addition ° C. | Remark | Ti (wt %) | Mg (wt %) | Donor (wt %) |
|---|---|---|---|---|---|---|---|
| ZN#102 | MGP#27 | 40 | 90 | | 4.5 | 15.2 | 19.3 |
| ZN#119 | MGP#45 | −5 | −5 | | 2.6 | 15.8 | 24.3 |
| ZN#120 | MGP#37 | −5 | −5 | | 3.3 | 18.7 | 10.5 |
| ZN#121 | MGP#37 | −5 | −5 | Three titanation @ 110° C. | 2.9 | 17.4 | 17.0 |
| ZN#129 | MGP#37 | −5 | −5 | two titanation @ 120° C. | 3.1 | 16.4 | 20.1 |
| ZN#131 | MGP#37 | −5 | −5 | Three titanation @ 120° C.— 1$^{st}$: 60 ml TiCl$_4$; 2$^{nd}$: 40 ml TiCl$_4$; 3$^{rd}$: 20 ml TiCl$_4$ | 2.8 | 17.5 | 17.0 |
| ZN#132 | MGP#37 | −5 | −5 | Three titanation @ 120° C. Two stage DIBP addition at 1$^{st}$ titanation— 1$^{st}$ @ −5° C.; 2$^{nd}$ @ 70° C. | 3.8 | 16.5 | 17.0 |
| ZN#133 | MGP#37 | −5 | −5 | Three titanation @ 120° C. | 2.7 | 16.7 | 20.5 |
| ZN#134 | MGP#37 | −5 | −5 | Three titanation @ 110° C. Two stage DIBP addition at 1$^{st}$ titanation— 1$^{st}$ @ −5° C.; 2$^{nd}$ @ 70° C. | 5.2 | 18.7 | 3.1 |
| ZN#135 | MGP#37 | −5 | −5 | Three titanation @ 110° C. | 2.5 | 18.0 | 13.6 |
| ZN#145 | MGP#37 | −5 | −5 | Three titanation @ 110° C.; TiCl$_4$(40 ml) | 3.0 | 18.2 | 12.5 |
| ZN#146 | MGP#37 | −5 | −5 | Three titanation @ 110° C.; Diether as internal donor | 4.9 | 11.9 | 17.5 |
| ZN#149 | MGP#64 | −5 | −5 | Three titanation @ 110° C. | 2.2 | 11.5 | 11.1 |

TABLE 2-continued

| Catalyst | Precursor | Precursor & TiCl₄ contact temperature ° C. | Internal donor addition ° C. | Remark | Ti (wt %) | Mg (wt %) | Donor (wt %) |
|---|---|---|---|---|---|---|---|
| ZN#150 | MGP#61 | −5 | −5 | Three titanation @ 110° C. | 2.3 | 17.5 | 15.4 |
| ZN#152 | MGP#37 | −5 | −5 | Three titanation @ 110° C. | 3.3 | 17.5 | 15.2 |
| ZN#153 | MGP#37 | −5 | −5 | Three titanation @ 110° C.; Temp ramping from −5° C. to 110° C. in 50 min | 2.5 | 18.6 | 14.4 |
| ZN#154 | MGP#66 | −5 | −5 | Three titanation @ 110° C. | 3.9 | 14.6 | 14.2 |
| ZN#156 | MGP#67 | −5 | −5 | Three titanation @ 120° C. | 2.5 | 15.9 | 14.4 |
| ZN#157 | MGP#66 | −5 | −5 | Three titanation @ 110° C.; (DIBP/Mg = 0.05 moles) | 3.1 | 18.1 | 8.7 |
| ZN#158 | MGP#67 | −5 | −5 | Three titanation @ 110° C.; (DIBP/Mg = 0.05 moles) | 1.8 | 15.7 | 17.7 |
| ZN#159 | MGP#66 | −5 | −5 | Three titanation @ 100° C.; (DIBP/Mg = 0.05 moles) | 2.8 | 17.5 | 12.2 |
| ZN#160 | MGP#66 | −5 | −5 | Three titanation @ 100° C.; (DIBP/Mg = 0.05 moles) | 3.1 | 17.1 | 12.2 |
| ZN#161 | MGP#66 | −5 | −5 | Three titanation @ 110° C.; (DIBP/Mg = 0.05 moles) | 1.1 | 16.8 | 14.5 |
| ZN#162 | MGP#66 | −5 | −5 | Three titanation @ 110° C. | 2.1 | 16.9 | 13.5 |
| ZN#164 | MGP#66 | −5 | −5 | Three titanation @ 110° C.; Additional chlorobenzene washing before hexane washing | 2.8 | 17.5 | 12.2 |
| ZN#165 | MGP#66 | −5 | −5 | Three titanation @ 110° C.; | 2.9 | 16.9 | 14.1 |
| ZN#168 | MGP#66 | −5 | −5 | Three titanation @ 110° C.; (Ti/Mg = 6.7 ) | 2.1 | 13.5 | 14.1 |
| ZN#169 | MGP#66 | −5 | −5 | Three titanation @ 110° C.; MGP dissolved in decane | 3.6 | 15.3 | |
| ZN#170 | MGP#66 | −5 | −5 | Three titanation @ 110° C.; MGP dissolved in mineral oil | 2.7 | 17.2 | |
| ZN#171 | MGP#66 | −5 | −5 | Three titanation @ 110° C.; (DIBP/Mg = 0.05 moles) | 2.9 | 18.5 | 12.7 |
| ZN#172 | MGP#66 | −5 | −5 | Three titanation @ 100° C. | 2.7 | 14.8 | 13.3 |
| ZN#173 | MGP#66 filtered | −5 | −5 | Three titanation @ 110° C. | 1.3 | 18.0 | 11.9 |
| ZN#175 | MGP#66 | −5 | −5 | Three titanation @ 110° C.; Charging of TiCl₄ to MGP/ID solution | 2.6 | 17.2 | 10.4 |
| ZN#176 | MGP#66 | −5 | −5 | Three titanation @ 110° C.; Charging of TiCl₄ to MGP/ID solution | 2.6 | 16.9 | 10.8 |
| ZN#179 | MGP#67 | −5 | −5 | Three titanation @ 110° C.; RPM 500 | 2.7 | 18.4 | 15.2 |

TABLE 2-continued

| Catalyst | Precursor | Precursor & TiCl₄ contact temperature ° C. | Internal donor addition ° C. | Remark | Ti (wt %) | Mg (wt %) | Donor (wt %) |
|---|---|---|---|---|---|---|---|
| ZN#180 | MGP#67 | −5 | −5 | Three titanation @ 110° C.; RPM 250 | 2.6 | 17.6 | |
| ZN#188 | MGP#75 | −5 | −5 | Three titanation @ 110° C. | 2.7 | 18.3 | 12.5 |
| ZN#189 | MGP#75 | −20 | −20 | Three titanation @ 110° C. | 2.4 | 16.7 | 14.4 |
| ZN#191 | MGP#75 | −20 | −20 | Three titanation @ 110° C.; Temp ramping from −20° C. to 110° C. in 60 min | 3.4 | 17.1 | |
| ZN#192 | MGP#75 | −20 | −20 | Three titanation @ 110° C.; Temp ramping from −20° C. to 110° C. in 120 min | 3.1 | 17.1 | 14.6 |
| ZN#193 | MGP#75 | −20 | −20 | Three titanation @ 110° C.; Temp ramping from −20° C. to 110° C. in 30 min | 3.0 | 17.4 | 13.6 |
| ZN#194 | MGP#75 | −20 | −20 | Three titanation @ 110° C.; Temp ramping from −20° C. to 110° C. in 120 min; RPM 250 | 3.1 | 17.1 | 15.5 |
| ZN#194 | MGP#75 | −20 | −20 | Three titanation @ 110° C.; Temp ramping from −20° C. to 110° C. in 120 min; RPM 175 | 2.5 | 17.3 | 14.2 |
| ZN#195 | MGP#75 | −20 | −20 | Three titanation @ 110° C.; Temp ramping from −20° C. to 110° C. in 120 min; RPM 750 | 2.2 | 16.0 | 16.1 |
| ZN#196 | MGP#76 | −20 | −20 | Three titanation @ 110° C.; Temp ramping from −20° C. to 110° C. in 120 min | 2.3 | 17.5 | 14.5 |
| ZN#207 | MGP#84 | −20 | −20 | Three titanation @ 110° C.; Temp ramping from −20° C. to 110° C. in 120 min | 1.3 | 15.5 | 11.2 |
| ZN#207 | MGP#83 | −20 | −20 | Three titanation @ 110° C.; Temp ramping from −20° C. to 110° C. in 120 min | 1.3 | 19.1 | 11.0 |
| ZN#209 | MGP#85 | −20 | −20 | Three titanation @ 110° C.; Temp ramping from −20° C. to 110° C. in 120 min | 1.8 | 18.5 | 9.3 |
| ZN#218 | MGP#75 | −20 | −20 | Three titanation @ 110° C.; Temp ramping from −20° C. to 110° C. in 120 min | 2.5 | 18.6 | 12.6 |
| ZN#288 | MGP#137 | −5 | −5 | Three titanation @ 110° C.; Temp ramping from −5° C. to 110° C. | 2.4 | 19.4 | 11.8 |

Table 2 represents the preparation of solid catalyst using organomagnesium compound as precursor under different reaction conditions.

Example 3

Slurry Polymerization of Propylene

Propylene polymerization was carried out in 1 L Buchi reactor which was previously conditioned under nitrogen. The reactor was charged with 250 ml of dry hexane containing solution of 10 wt % triethylaluminum followed by 100 ml of dry hexane containing 10 wt % solution of triethylaluminum, 5 wt % solution of cyclohexy methyl dimethoxysilane and weighed amount of catalyst. The reactor was pressurized with hydrogen to 60 ml then charged with 71 psi of propylene under stirring at 750 rpm. The reactor was heated to and then held at 70° C. for 2 hour. At the end, the reactor was vented and the polymer was recovered at ambient conditions.

Catalyst performance and polymer properties has been tabulated in Table 3

TABLE 3

| Cat No | Cat wt (mg) | Al/Ti ratio | H2 ml | Al/Do ratio | Activity kgPP/gcat | MFI @ 2.16 kg | XS wt % | BD g/cc |
|---|---|---|---|---|---|---|---|---|
| ZN#102 | 15.5 | 250 | 10 | 20 | 5.8 | — | 4.2 | |
| ZN#121 | 14.2 | 500 | 10 | 20 | 11 | — | 2.0 | 0.41 |
| | 10.5 | 500 | 10 | 20 | 13.3 | 5.3 | 3.2 | 0.40 |
| | 10.5 | 500 | 10 | 30 | 14.3 | 4.8 | 3.7 | 0.41 |
| | 10.3 | 500 | 10 | 10 | 13.2 | 4.1 | 2.1 | 0.40 |
| | 10.2 | 500 | 10 | 5 | 12.4 | 3.6 | 5.5 | 0.42 |
| | 10.2 | 500 | 10 | 40 | 10.4 | — | 6.6 | 0.41 |
| | 10.6 | 500 | 0 | 30 | 7.7 | — | 4.2 | 0.40 |
| ZN#129 | 10.6 | 500 | 10 | 20 | 10.6 | 2.6 | 3.0 | 0.27 |
| ZN#131 | 10.6 | 500 | 10 | 20 | 6.9 | 2.5 | 2.0 | 0.36 |
| ZN#132 | 10.3 | 500 | 10 | 20 | 15.1 | 3.9 | 3.2 | 0.35 |
| ZN#133 | 10.2 | 500 | 10 | 20 | 13.5 | 2.4 | 2.1 | 0.43 |
| ZN#135 | 10.4 | 500 | 10 | 20 | 10.8 | 0.5 | 1.9 | 0.38 |
| ZN#145 | 10.5 | 500 | 10 | 20 | 9.9 | 2.1 | 2.6 | 0.37 |
| ZN#149 | 10.8 | 500 | 10 | 20 | 9.5 | 2.2 | 1.6 | 0.38 |
| ZN#154 | 10.3 | 500 | 10 | 20 | 12.8 | 6.0 | 1.9 | 0.34 |
| ZN#156 | 10.2 | 500 | 10 | 20 | 12.7 | 1.6 | 2.5 | 0.36 |
| ZN#157 | 10.0 | 500 | 10 | 20 | 14.7 | 5.4 | 2.5 | 0.38 |
| ZN#158 | 10.3 | 500 | 10 | 20 | 7.1 | 3.6 | 2.1 | 0.37 |
| ZN#159 | 10.5 | 500 | 10 | 20 | 8.6 | 3.4 | 2.2 | 0.39 |
| ZN#160 | 10.0 | 500 | 10 | 20 | 11.7 | 3.0 | 2.0 | 0.40 |
| ZN#161 | 15.0 | 500 | 10 | 20 | 9.8 | 2.4 | 2.0 | 0.32 |
| ZN#162 | 10.3 | 500 | 10 | 20 | 9.0 | 2.7 | 2.0 | 0.34 |
| ZN#164 | 10.3 | 500 | 10 | 20 | 7.8 | 3.7 | 1.6 | 0.35 |
| ZN#165 | 10.6 | 500 | 10 | 20 | 12.5 | 8.8 | 1.2 | 0.41 |
| ZN#168 | 10.3 | 500 | 10 | 20 | 9.0 | 2.6 | 1.1 | 0.33 |
| ZN#169 | 10.7 | 500 | 10 | 20 | 8.3 | 3.2 | 1.5 | 0.33 |
| ZN#170 | 10.8 | 500 | 10 | 20 | 6.3 | 5.6 | 1.1 | 0.32 |
| ZN#171 | 10.3 | 500 | 10 | 20 | 10.8 | 2.2 | 1.3 | 0.38 |
| ZN#172 | 10.2 | 500 | 20 | 20 | 9.0 | 4.0 | 1.9 | 0.32 |
| ZN#173 | 10.9 | 500 | 10 | 20 | 1.8 | 1.6 | 2.5 | 0.31 |
| ZN#175 | 10.1 | 500 | 10 | 20 | 13.0 | 2 | 1.8 | 0.43 |
| ZN#176 | 10.6 | 500 | 10 | 20 | 13.7 | 3.4 | 1.3 | 0.42 |
| ZN#179 | 10.7 | 500 | 10 | 20 | 10.2 | 2.8 | 1.9 | 0.27 |
| ZN#180 | 10.0 | 500 | 10 | 20 | 11.2 | 2.4 | 2.3 | 0.29 |
| ZN#189 | 10.4 | 500 | 10 | 20 | 8.3 | 2.7 | 2.0 | 0.32 |
| ZN#188 | 10.3 | 500 | 10 | 20 | 11.3 | 3.0 | 1.7 | 0.36 |
| ZN#191 | 10.6 | 500 | 10 | 20 | 10.6 | 2.3 | 1.7 | 0.32 |
| ZN#192 | 10.2 | 500 | 10 | 20 | 11.9 | 3.2 | 2.2 | 0.37 |
| ZN#193 | 10.2 | 500 | 10 | 20 | 9.5 | 4.7 | 1.7 | 0.33 |
| ZN#194 | 10.4 | 500 | 10 | 20 | 9.3 | 8.6 | 1.9 | 0.31 |
| ZN#195 | 10.7 | 500 | 10 | 20 | 10.1 | 3.3 | 1.4 | 0.35 |
| ZN#196 | 10.0 | 500 | 10 | 20 | 10.5 | 4.2 | 2.3 | 0.32 |
| ZN#207 | 10.8 | 500 | 10 | 20 | 7.6 | 7.2 | 2.9 | 0.37 |
| ZN#208 | 10.8 | 500 | 10 | 20 | 0.8 | 4.5 | 3.1 | 0.35 |
| ZN#209 | 10.8 | 500 | 10 | 20 | 9.7 | 3.1 | 2.3 | 0.37 |
| ZN#288 | 10.0 | 500 | 10 | 30 | 5.5 | 5.3 | 3.6 | 0.45 |

Table 3 represents the propylene polymerization using different catalyst synthesized using different organomagnesium compounds as precursors. The catalysts synthesized under different conditions were found to be active for propylene polymerization.

We claim:

1. A process for preparation of a catalyst composition, said process comprising:
   (a) contacting a solution of transition metal compound represented by $M(OR''')_p X_{4-p}$, where M is a transition metal and is selected from the group consisting of Ti, V, Zr, and Hf; X is a halogen atom; R''' is a hydrocarbon group and p is an integer having value equal or less than 4, with a solid organomagnesium precursor having formula $\{Mg(OR')X\}.a\{MgX_2\}.b\{Mg(OR')_2\}.c\{R'OH\}$, wherein R' is selected from a hydrocarbon group, X is selected from a halide group, and a:b:c is in range of 0.01-0.5:0.01-0.5:0.01-5 to obtain a resulting solution, and contact temperature of solid organomagnesium precursor and the transition metal compound is between about −50° C. and about 150° C.;
   (b) prior to step (a), adding an internal donor either to the solid organomagnesium precursor component or to the titanium component, and the contact time of the said component with the internal donor is immediate or is at least 1 minutes to 60 minutes at contact temperature of between about −50° C. and about 100° C.;
   (c) treating the resulting solution obtained in the step (a) with a solution comprising a titanium component in a solvent and recovering a solid titanium catalyst component and maintaining the recovered solid titanium catalyst component at a temperature value in the range of 100 to 120° C. for about 10 to 60 minutes; and
   (d) optionally repeating step (c) for a predetermined number of times and then washed sufficiently with inert solvent at temperature 20° C. to 80° C. to obtain a solid catalyst composition,
   wherein the solid organomagnesium precursor is prepared by a process comprising contacting a magnesium source with a solvating agent, an organohalide and an alcohol to obtain the solid organomagnesium precursor, wherein the solvating agent is selected from the group consisting of dimethyl ether, diethyl ether, dipropyl ether, diisopropyl ether, ethylmethyl ether, n-butylmethyl ether, n-butylethyl ether, di-n-butyl ether, diisobutyl ether, isobutylmethyl ether, and isobutylethyl ether, dioxane, tetrahydrofuran, 2-methyl tetrahydrofuran, tetrahydropyran and combination thereof.

2. The process as claimed in claim 1, wherein in step (a) the transition metal compound is added to the organomagnesium compound or organomagnesium compound is added to transition metal compound.

3. The process as claimed in claim 1, wherein step (b) comprises adding organomagnesium precursor with internal donor.

4. The process as claimed in claim 1, wherein transition metal is titanium metal.

5. The process as claimed in claim 1, wherein the transition metal compound represented by $M(OR''')_p X_{4-p}$ is selected from the group consisting of transition metal tetrahalide, alkoxy transition metal trihalide or aryloxy transition metal trihalide, dialkoxy transition metal dihalide, trialkoxy transition metal monohalide, tetraalkoxy transition metal, and mixtures thereof; wherein:
   (a) the transition metal tetrahalide is selected from the group consisting of titanium tetrachloride, titanium tetrabromide, titanium tetraiodide, vanadium tetrachloride, vanadium tetrabromide, vanadium tetraiodide, zirconium tetrachloride, zirconium tetrabromide, zirconium tetraiodide, hafnium tetrachloride, hafnium tetrabromide, and hafnium tetraiodide;
   (b) alkoxy transition metal trihalide or aryloxy transition metal trihalide is selected from the group consisting of methoxytitanium trichloride, ethoxytitanium trichloride, butoxytitanium trichloride, phenoxytitanium trichloride, methoxyvanadium trichloride, ethoxyvanadium trichloride, butoxyvanadium trichloride, phenoxyvanadium trichloride, methoxyzirconium trichloride, ethoxyzirconium trichloride, butoxyzirconium trichloride, phenoxyzirconium trichloride, methoxyhafnium trichloride, ethoxyhafnium trichloride, butoxyhafnium trichloride, and phenoxyhafnium trichloride;
   (c) dialkoxy transition metal dihalide is selected from the group consisting of diethoxy titanium dichloride, diethoxy vanadium dichloride, diethoxy zirconium dichloride, and diethoxy hafnium dichloride;

(d) trialkoxy transition metal monohalide is selected from the group consisting of triethoxy titanium chloride, triethoxy vanadium chloride, triethoxy zirconium chloride, and triethoxy hafnium chloride; and (e) tetraalkoxy transition metal is selected from the group consisting of tetrabutoxy titanium, tetraethoxy titanium, tetrabutoxy vanadium, tetraethoxy vanadium, tetrabutoxy zirconium, tetraethoxy zirconium, tetrabutoxy hafnium, and tetraethoxy hafnium.

6. The process as claimed in claim 1, wherein the internal electron donor used is selected from the group consisting of phthalates, benzoates, succinates, malonates, carbonates, diethers, and combinations thereof; wherein:

(a) the phthalate is selected from the group consisting of di-n-butyl phthalate, di-i-butyl phthalate, di-2-ethylhexyl phthalate, di-n-octyl phthalate, di-i-octyl phthalate, di-n-nonyl phthalate;

(b) the benzoate is selected from the group consisting of methyl benzoate, ethyl benzoate, propyl benzoate, phenyl benzoate, cyclohexyl benzoate, methyl toluate, ethyl toluate, p-ethoxy ethyl benzoate, p-isopropoxy ethyl benzoate;

(c) the succinate is selected from the group consisting of diethyl succinate, di-propyl succinate, diisopropyl succinate, dibutyl succinate, diisobutyl succinate;

(d) the malonate is selected from the group consisting of diethyl malonate, diethyl ethylmalonate, diethyl propyl malonate, diethyl isopropylmalonate, diethyl butylmalonate;

(e) the carbonate compound is selected from the group consisting of diethyl 1,2-cyclohexanedicarboxylate, di-2-ethylhexyl 1,2-cyclohexanedicarboxylate, di-2-isononyl 1,2-cyclohexanedicarboxylate, methyl anisate, ethyl anisate; and (f) the diether compound is selected from the group consisting of 9,9-bis(methoxymethyl)fluorene, 2-isopropyl-2-isopentyl-1,3-dimethoxypropane, 2,2-diisobutyl-1,3-dimethoxypropane, 2,2-diisopentyl-1,3-dimethoxypropane, 2-isopropyl-2-cyclohexyl-1,3-dimethoxypropane.

7. The process as claimed in claim 1, wherein in step (a) the contact of organomagnesium compound with titanium compound is either neat or in solvent.

8. The process as claimed in claim 1, wherein in step (a) the solid organomagnesium compound is used as solid or in solvent.

9. The process as claimed in claim 7, wherein the solvent is selected from the group consisting of chlorinated aromatic hydrocarbon, non chlorinated aromatic hydrocarbon chlorinated aliphatic hydrocarbon, non chlorinated aliphatic hydrocarbon and combination thereof.

10. The process as claimed in claim 7, wherein the solvent is comprising from 5 to 95 volume percent and is selected from the group consisting of benzene, decane, kerosene, ethyl benzene, chlorobenzene, dichlorobenzene, toluene, o-chlorotoluene, xylene, dichloromethane, chloroform, cyclohexane and combination thereof.

11. The process as claimed in claim 1, wherein in step (b) the internal electron donor is used in an amount of from 0.01 to 0.5 moles, with respect to one mole of magnesium.

\* \* \* \* \*